(12) United States Patent
Ruppenthal

(10) Patent No.: US 6,177,018 B1
(45) Date of Patent: Jan. 23, 2001

(54) DOSING MECHANISM TO FEED GERMICIDE OR DISINFECTANT INTO A WATER SUPPLIED SUPPLY DEVICE AND THE USE THEREOF

(75) Inventor: Mathias Ruppenthal, Bruchsal (DE)

(73) Assignee: Alpro-Dental Produkte GmbH (DE)

( * ) Notice: Under 35 U.S.C. 154(b), the term of this patent shall be extended for 0 days.

(21) Appl. No.: 09/269,440

(22) PCT Filed: Sep. 25, 1997

(86) PCT No.: PCT/DE97/02190

§ 371 Date: Jan. 7, 2000

§ 102(e) Date: Jan. 7, 2000

(87) PCT Pub. No.: WO98/13074

PCT Pub. Date: Apr. 2, 1998

(30) Foreign Application Priority Data

Sep. 27, 1996 (DE) .............................................. 196 39 666

(51) Int. Cl.[7] ...................................................... C02F 1/50
(52) U.S. Cl. ..................... 210/739; 210/752; 210/764; 210/96.1; 210/101; 210/136; 210/143; 210/198.1; 422/3; 422/28; 422/110; 422/256; 433/88; 433/98; 433/229
(58) Field of Search ................................... 210/739, 749, 210/752, 764, 765, 96.1, 101, 143, 136, 192, 198.1, 205, 206; 422/3, 28, 37, 108, 110, 256; 433/88, 98, 229

(56) References Cited

U.S. PATENT DOCUMENTS

| | | | |
|---|---|---|---|
| 4,545,956 | * 10/1985 | Ciszewski et al. | 422/28 |
| 5,366,693 | * 11/1994 | Burgos et al. | 422/26 |
| 5,526,841 | * 6/1996 | Detsch et al. | 137/15 |
| 5,709,546 | * 1/1998 | Waggoner | 433/82 |
| 5,837,204 | * 11/1998 | Prevost et al. | 422/105 |
| 5,976,386 | * 11/1999 | Barak | 210/756 |
| 6,019,117 | * 2/2000 | Detsch et al. | 137/15 |
| 6,027,572 | * 2/2000 | Labib et al. | 134/8 |

FOREIGN PATENT DOCUMENTS 34 03 640 A1   8/1985 (DE) .
43 10 264 A1  10/1994 (DE) .

OTHER PUBLICATIONS

Technisches Handbuch–Wasseraufbereitungsanlagen, VEB–Verlag Technik Berlin, 1966, p. 659, figure 6.94.

J. Mutschmann, "Taschenbuch der Wasserversorgung" 9th edition, Stuttgart, Franckh'sche Verlagshandlung, 1986, Kap. 5.4.2.1.1.

* cited by examiner

Primary Examiner—Peter A. Hruskoci
(74) Attorney, Agent, or Firm—Pendorf & Cutliff

(57) ABSTRACT

Dosing mechanism to feed germicide or disinfectant into a water supplied supply device in order to provide disinfected water for consumers. Said dosing mechanism comprises a disinfectant storage tank (12), pathway for water flow (20) leading to at least one junction point (30), a remote-controlled feeder (22) enabling germicide to be added, a control device (52) working together with a flow metro which detects flow volume of water supplied and transmitting it as a signal to the control device (52) which actuates the feeder (22) according to a predefinable concentration of germicide in water. The storage tank (12) is pressurized with compressed air and the feeder is designed as a proportional valve (22) which can be actuated by the control device.

17 Claims, 4 Drawing Sheets

DOSING MECHANISM TO FEED GERMICIDE OR DISINFECTANT INTO A WATER SUPPLIED SUPPLY DEVICE AND THE USE THEREOF

BACKGROUND OF THE INVENTION

1. Field of the Invention

The invention concerns a dosing device for introducing germicide or disinfectant into a water-supplied supply device for making aseptic or disinfected water available to users.

2. Description of the Related Art

It is generally known to disinfect water by addition of certain chemical substances. In these cases it is conventional to add germicides or disinfectants in tablet form or, in larger amounts, as solutions to the water to be disinfected in order to achieve a better mixing of the water to be disinfected. Independent of the type of addition, for the desired germicidal or disinfecting action attention must be given to make sure that a good mixing of the water with the germicide or disinfectant occurs.

A common environment of use is in the disinfecting of water needed by patients for dental hygiene in dental practices, for example for rinsing out the mouth.

Conventionally, dosing devices are employed for this, with which the water is periodically injected or inoculated. This means that the disinfectant is added at regular periods, since this device largely works on the basis of clocked magnets, which are associated with the pumps and/or valves employed therefor.

These types of components allow only large switch intervals, so that the intervals between the individual injections are correspondingly large. This results in substantial fluctuations in the concentration of the disinfectant in the water.

A further known device includes a supply container for disinfectant charged with compressed air, which is connected with a receiver via an appropriate pipe or hose conduit. In this delivery path a remote operable inlet valve for the disinfectant is provided, which controls the introduction of the disinfectant into the flow path of the water which goes to the receiver. Upon activation of the receiver this supply valve opens and in inactive times it is closed.

A particularly high volume concept of the water is not envisioned in this device. The mixing in of the disinfectant occurs with the help of a periodic magnet valve, of which the opening occurs periodically cyclically, as soon as the dispenser, for example pouring water into a glass for rinsing the mouth, is switched on, that is, as upon activation of the outflow. Here also fluctuations on concentration are unavoidable.

Finally there is known from DE 34 03 640 A1 a dosing device, which is the starting point of the present invention. In this device the disinfectant is introduced into the water in a special mixing chamber, which is incorporated in the supply conduit. The pressure conduit of a disinfectant conveying piston pump discharges into this mixing chamber.

For the purposes of dosing a control device is provided, which acts upon the piston pump in correspondence to the flow amount or, as the case may be, the flow velocity in the supply conduit, so that the desired amount of disinfectant is conveyed out of the supply container. The control of the piston pump can be achieved either by the rotation count of the drive motor or the transmission relationship of the reduction gear mechanism, in order to appropriately adapt the pressure stroke of the pump.

It has been found to be a disadvantage herein that the disinfecting action of the germicide is substantially limited in range to the mixing chamber itself. With longer periods of inactivity, as are conventional in the dental practice for example during two sequential days of the weekend, there exits the danger that the disinfecting action is reduced and impermissibly high contamination values occur. Further there occurs the problem, that in the course of the normal useage dead bacteria and other organic substances adhere as the so-called bio-film in the area of the supply conduit and in the downstream water conveying paths, which is an ideal nutrient supply for further germ growth. It is thus necessary to undertake a complete sterilization (basic- or intensive disinfecting) at regular intervals.

To do this the device must be taken out of commission. Thereafter the various hose connections must be released and there follows the connection to a separate pump system, which is specially provided for the complete disinfecting and the treatment with a 100% concentration of disinfectant introduced with the objective of removing the bio-film and sanitizing the water supply elements. Thereafter the conduit system must be rinsed with clean water, in order to avoid a subsequent unacceptably high concentration of disinfectant at the resumption of operation. A cleansing process of this type is time and cost consuming.

Further, the construction cost for this type of device is substantial, since besides the mixing chamber to be employed in the supply line, the piston pump in particular inclusive of its controls is relatively complicated. Besides the necessity to influence the rotation and/or the transmission relationship of the drive there must be provided special precautions in the form of over-pressurization valves and return conduits, in order to assure functional safety.

Finally, there occurs also in this device the undesirable fluctuations in concentration of germicide in the water, since the piston pump cyclically introduces the germicide corresponding to the stroke volume of the piston pump.

Beginning with this state of the art it is the task of the invention to provide a dosing device of the above-described type, which is simple in construction and easy to operate and which insures an addition of germicide corresponding to the requirements.

SUMMARY OF THE INVENTION

In invention is based upon the idea of completely dispensing with the pump inclusive of its complicated control, and in place of this to provide a simple supply container which can be charged with compressed air, and to achieve the addition of germicide/disinfectant via a proportional valve controlled by a control unit. Besides the simplified construction associated therewith, there results a constant addition of germicide/disinfectant material into the water flowing by. Concentration fluctuations, as had been presumed to be unavoidable in all previous dosing devices, no longer occur here. Herewith there can be achieved a secure and reliable disinfecting with reduced amounts of germicide/disinfectant.

The required conveyance pressure, with which the supply container is to be charged, can most economically be found in the environment in which this type of dosing device is to be operated. As an example, there can be mentioned the pressure air connection for the drive means for a drill turbine of a dental unit.

Beyond this, the mixing chamber can be completely dispensed with since the disinfectant can preferably be introduced directly into the supply line via the proportional valve. Because of the small space requirement of the proportional valve it is possible to provide the introduction point immediately adjacent the work place, so that contamination hardly ever occurs even in the case of longer periods of nonuse.

As proportional valve, preferred is a piezoelectric valve, which can be constructed particularly compactly and besides this is reliably controllable.

According to a further preferred embodiment of the invention the proportional valve is controllable through the control device such that the concentration of disinfectant is adjustable variably between 0% and 100%. Therewith it is possible to carry out the intensive sanitation which is required from time to time without any particular or supplemental measures. The proportional valve is so controlled in connection with the supply valve for the water, that the water supply can be completely blocked and subsequently disinfectant can be released. For the subsequent rinsing process it is essentially only necessary that the introduction of disinfectant halted, so that pure water can flow. The switching of these operating conditions occurs by the control device, wherein no further construction components or reconfiguration is necessary.

According to a further preferred embodiment a device is provided for determination of the actual value of the concentration downstream of the introduction point, which is connected with the control device for a closed circuit or control feedback loop. Therewith the actual achieved concentration can be continuously monitored and maintained to a constant precise value.

Further, a dosing device is preferred which includes a device for self-calibration, in order to counteract indications of age or changes in the response relationship of the proportional valve even after longer periods of use. It is envisioned, that the self-calibration can be allowed to occur automatically at certain, fixed, pre-determined time intervals or also automatically after longer periods of inactivity.

According to a further embodiment of the invention the introduction of the germicide is provided in the flow path of the treated water upstream of the flow meter.

Herein it is advantageously taken advantage of, that the flow meter improves at least a rotational body, for example an impeller, worm wheel or propeller, which thoroughly mixes the supply or feed water and the introduced germicide and thereby uniformly mixes these with each other.

In a useful embodiment of the invention the inlet of the germicide is provided in the flow path of the feed water in the area of the user.

According to a further preferred embodiment a recoil or backflow valve is provided between the point of the introduction of the germicide into the flow path of the water and the supply container, which effectively precludes the admission of water into the supply container. Further, a filter device is preferably also provided between the point of the introduction of the germicide into the flow path of the water and the supply container, which precludes the admission of impurities and/or clumps from the supply container, which would adversely impact the mixing and solubility in water.

In the case that greater than conventional amounts of germicide are needed, a second conduit with a second feed valve for the introduction of the germicide into the stream or flow of the water can be provided, which operates parallel to the first feed valve, and which brings about a more rapid introduction of the germicide at a second introduction point and is position, for example, down stream of the first introduction point.

Further preferred variations are concerned with the concept of an integrated buffer storage for sanitized water. So it can be necessary, in the case of strongly septic water, to increase the dwell time of the germicide to be dosed. For each type of germ a different residence time of the germicide is necessary. A buffer zone or buffer space insures, even in heavy use, the maintenance of the necessary dwell time between dosing and outflow at the instrument end. The buffer zone or buffer storage offers a possibility for this by increasing the dwell time of the germicide treated water.

It is preferred when the buffer storage area is constructed of a packet of tubes, which for example is comprised of a plurality of flat tubes positioned adjacent to each other. It is particularly space saving when the bundle of tubes has a rectangular or quadratic cross-section, so that the flow cross-section is optimally utilized. The tube packet is closed at the respective end pieces for the formation of a through-going flow path, wherein the end pieces exhibit apertures or through holes of the type, such that a fluid-tight, respective pair-wise connection of two adjacent tubes results.

It is preferred that the buffer storage area is introduced in a receptacle housing, so that a supplemental module is formed, which can be placed either immediately on the housing of the dosing device or alternatively can be positioned downstream of the dosing device.

In a preferred embodiment the inventive dosing device is formed as an add-on module, which is integratable into an existing dental hygiene apparatus.

The inventive dosing devices are preferably employed with devices for dental hygiene, for example in dental equipment used in the dental practice. In contrast to the known devices of this type, the determination of the amount of germicide or disinfectant to be introduced is based exclusively upon the amount of water flowing through. From this it follows, that the taking into consideration of further factors, for example the environment and the pressure, in which the inventive dosing device is to be employed, is not necessary for the function thereof. The retrofitting of existing dental units which do not have disinfection capability is therewith economically possible. Likewise, the inventive dosing device is suitable for dosing of similar substances, such as for example cleansing substances.

BRIEF DESCRIPTION OF THE DRAWINGS

On the basis of a schematic represented embodiment of the invention, the invention including preferred embodiments and improvements as well as particular advantages thereof will be described in greater detail. There are shown.

DETAILED DESCRIPTION OF THE INVENTION

Figure 1:
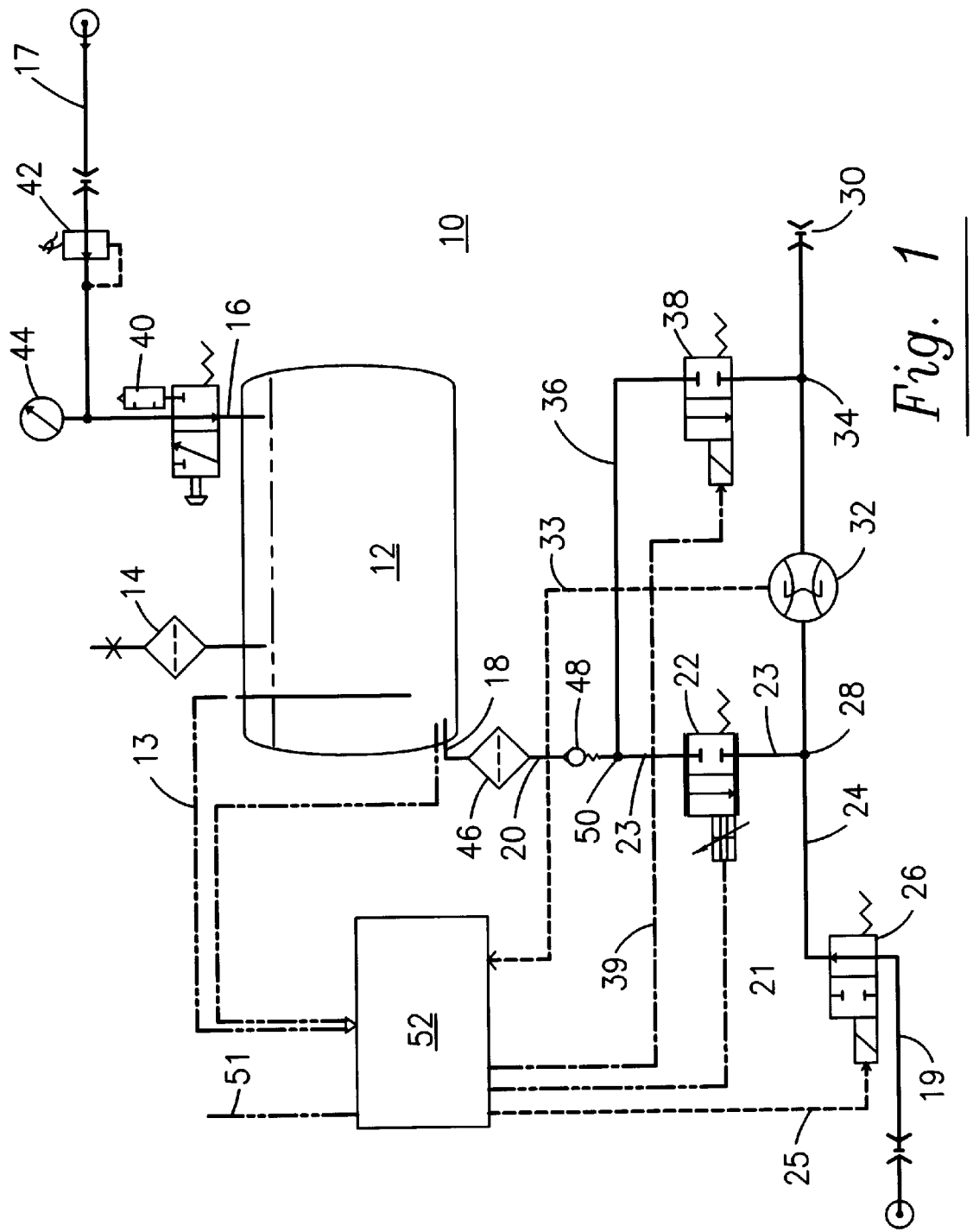
FIG. 1 schematic diagram for a circuit arrangement of a dosing device according to the invention.

In FIG. 1 a dosing device 10 is shown with a supply container 12 for fluid disinfectant, wherein the supply container 12 is provided on its upper side with a, here only diagrammatically represented, refill pipe with integrated strainer 14, through which the filling of the supply container 12 with disinfectant occurs.

Further, the supply container 12 includes on its upper side a connection pipe 16 for the pressure line 17, by means of which the supply container 12 is charged and internally pressurized.

Thereby it is ensured that the disinfectant can stably flow out of the supply container 12.

For this purpose an outlet pipe 18 is provided on one side, which in FIG. 1 is the left side, which is connected with a supply line 20, which leads to a first supply valve 22 constructed as a proportional valve. This first supply valve 22 is constructed as an electrically operable proportional valve to introduce the amount of the disinfectant to be supplied via the first supply line 23 into a water pipeline 24.

The water pipeline 24, in which likewise an electrically operable valve 26 is provided, leads from a not shown supply network to a junction point 30 for one or more, here likewise shown, users.

In the water pipeline 24 of the pipeline segment shown in FIG. 1 there is to be found a first inlet point 28 for a first supply line 23 for disinfectant.

Downstream of this inlet point 28 there is provided a flow meter device 32, which via a signal circuit 33 is connected with acentral control unit 52, which via line 51 is supplied with electrical energy from a here not shown electrical supply network, and which flow meter measures the amount of water flowing through inclusive of the introduced disinfectant and transmits this to the central control unit 52. Herein it is to be noted that the amount of disinfectant is in the range of 1 to 2% and thus is of negligible influence on the determination of the flow amount of water.

Beyond this it is possible, by appropriate programming, to adapt the recognition signal, for example, by an appropriate compensation equation, to factor out this small addition amount of disinfectant.

Further it is possible using circuit technology to close the supply valve 22 formed as a proportional valve for a short period of time for several milliseconds prior to making each measurement value, the behavior of the valve being similar to a condenser, in order to empty this prior to controlling with the new voltage or signal. Thereby a drift of the actual value is precluded. Since the removal of treated water respectively occurs for only a short period of time and the addition of disinfectant occurs during this interval of operation, it is also possible in this way that the potential occurrence of a drift dependent small actual value variation or deviation can likewise be disregarded.

Between the flow meter 32 and the junction point 30 for the one or more users there is provided a further introduction point 34 for disinfectant. This introduction point 34 is connected via a second supply line 36, in which a second, likewise electrically operable, supply valve 38 is provided.

The manner of operation of this dosing device 10 is as follows. The supply container 12 is filled via fill pipe 14 with disinfectant. The therein integrated filter serves to prevented the entry of impurities into the dosing device. In order to make possible the filling with disinfectant, the previously discussed pressurized air supply via the feed pipe 16 or, as the case many be, via the thereon connected line 17, is blocked by operation of an appropriate closure means 40, valve, or slide and the supply container 12 is without pressure.

As soon as the supply container 12 is sufficiently filled with disinfectant, the fill pipe 14 is closed pressure tight.

Now the pressure air valve 40 is opened, so that the pressure air from line 17 enters into the supply container 12 via the pressure air feed pipe 16 and charges the therein situated disinfectant with pressure. A pressure regulator 42 provided in the pressure supply line 17 regulates the air pressure, which is between approximately 0.4 to 0.5 Mpa, to approximately, for example, 0.3 MPa and insures thereby for an even pressurization in the supply container 12 as well as therefore, that the supply container 12 experiences no impermissible stresses from a too-high over-pressurization. A likewise provided manometer 44 for control shows the actual pressure. Herein it is to be noted, that for the problem-free operation the pressure value in the supply container 12 must consistently be sufficiently above the pressure of the water.

Via the outlet pipe 18 positioned at the end close to the ground the disinfectant proceeds via the supply line 20 first to a therein situated fine filter 46 which retains any fine impurities and/or clumps of the disinfectant, which would detract from the solubility in water. Downstream there follows a back-flow valve 48, which prevents a reversal of flow into the line 20 and therewith prevents entry of water into the supply container.

Behind the back-flow valve 48 there is a branching 50. From there the first supply line 23 runs to the first supply valve 22 and the second supply line 36 runs to the second supply valve 38.

Depending upon the value of the flow volume determined by the flow meter 32 a signal is transmitted to the central control unit 52, which processes this signal and therefrom determines the opening, that is the width of the opening, of the first supply valve 22 and controls this via a control line 21.

In the same way water valve 26 is controlled by a control circuit 25. Likewise the degree of fill of the supply container 12 is transmitted via signal circuit 13 to the central control unit 52. The central control unit 52 serves both for monitoring and determining all relevant operational parameters as well as for the optimal process control of the individual valves.

In the case that a particularly large amount of disinfectant is to be introduced, for example for basic sterilization, then supplemental disinfectant can be introduced into the water supply line 24 through the second supply 36 via the second supply valve 34 connected to the central control unit 52 via control circuit 39. This can also be combined with a blockage of the water line 24 via valve 26.

The addition or introduction of the disinfectant occurs as previously discussed, upstream of the flow meter, so that a better mixing of the disinfectant with the water to be disinfected is achieved. Beyond this it is possible that in certain cases additives are added to the disinfectant, such as for example for preventing the depositing of calcium and algae, as well as for further reducing the surface tension, to improve the effectiveness of the flow meter and thus insure a problem free operation for the longest possible period of time.

For self-calibration the control unit 52 blocks the water valve 26. Thereby there is produced between the supply container 12 and the junction point 30 the pressure existing in the supply container 12 as pressure gradient, in order to allow the disinfectant to flow with an elevated flow rate through the valve 26 and the flow meter 32 upon opening by a user.

The control unit 52 sequentially sends at least three fixed different voltage values to the valve 26, which opens in response. Via the flow meter 32 the control unit 52 detects the actual flow rate, calculates the deviation from the prescribed characteristic curve (flow rate in dependence from valve voltage) and determines correction values for the adjustment of the characteristic curve. This correction values are stored (EEPROM) and are available until the next calibration process, in order to achieve the actual index values for the intended voltage for the valve 26.

Figure 2:
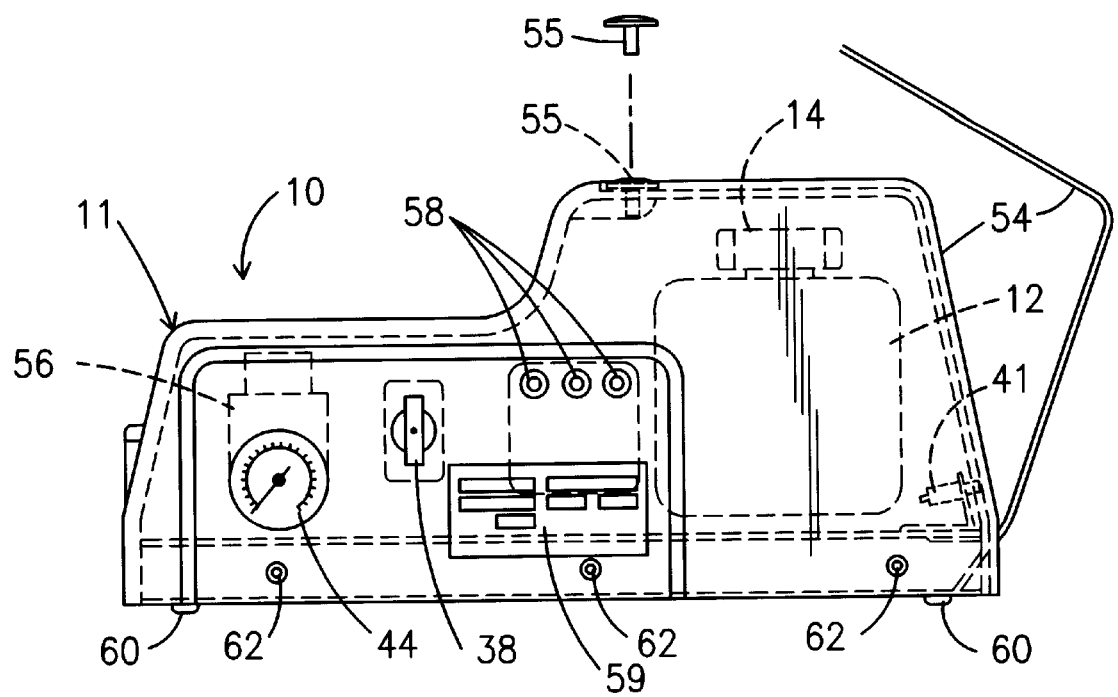
FIG. 2 side view of an inventive dosing device.
Figure 3:
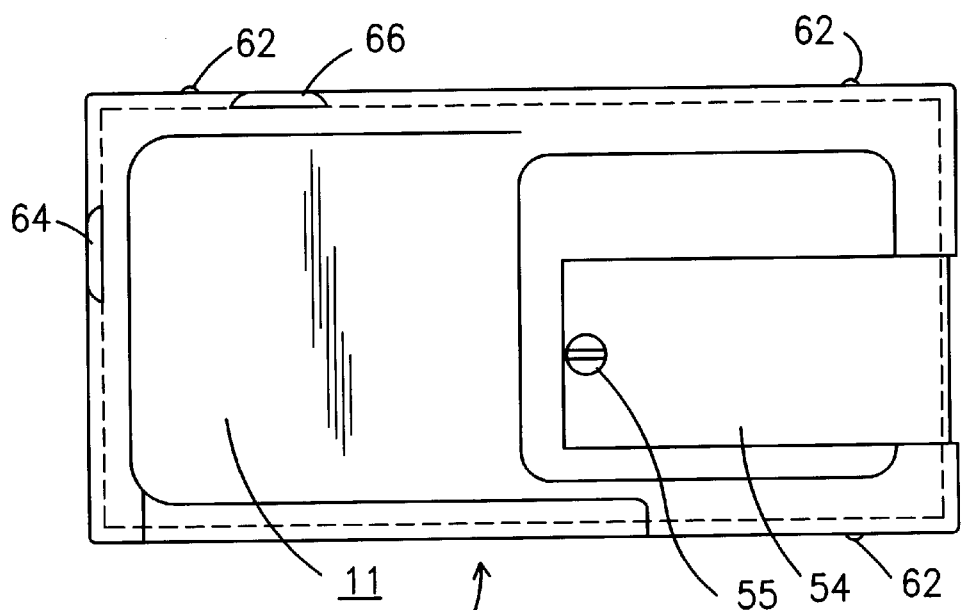
FIG. 3 top view of the dosing device according to FIG. 2.

In FIG. 2 a practical constructed device of an inventive dosing device 10 is shown in side view, from which representation it is possible to recognize the very compact and at the same time very useful design. The representation in the further FIGS. 3 and 4 clarify the compact shape of the housing 11.

The inventive device 10 includes a housing 11, of which the wall is preferably comprised of an anti-static plastic which is easy to take care of and clean, for example polyurethane, and of which the inner side cross-section can be recognized from the indicated dashed lines. The housing 11 is formed step-shaped and possesses a flat area and an elevated area. The elevated area, which is on the right side in FIG. 2, is covered by a pivotable folding lid coupled or hinged on the lower right end side of the housing 11, which lid is held in the rest position by a screw lock mechanism 55 and which makes possible in a simple manner to have rapid access to the supply container 12 situated inside of the housing 11, in order, for example, to fill it.

In FIG. 2 the supply container 12 is represented with broken lines, since in this view it is covered by the side wall and thus under normal conditions not visible. Likewise represented with broken lines is the filling connection pipe with filter 14 positioned above the supply container 12. On the right side of the housing 11 an exhaust valve 41 is positioned covered by the folding lid 54, which exhaust valve is preferably integrated in the air pressure valve 40.

Below this, on the front surface of the flat area of the housing 11, that is, in the plane of the drawing, there are the control elements for setting the device or, as the case may be, for adjusting the operating perimeters, are provided on a control panel 56 easily accessible and visible.

Individually on the control panel 56 are provided the Manometer 44 and the second supply valve 38, which is shown here as a manually operated magnetic valve, as well as three light indicators 58, which are preferably constructed as LEDs. Finally, a model identification plate 59 is provided on the panel 56.

On the lower side of the housing 11 there are provided base feet 60, preferably of rubber, upon which the device is set up substantially sound insulated. Further, mounting screws 62 for securing the housing 11 are provided on the sides of the housing 11, by means of which a securing or mounting within a larger device is possible.

Figure 4:
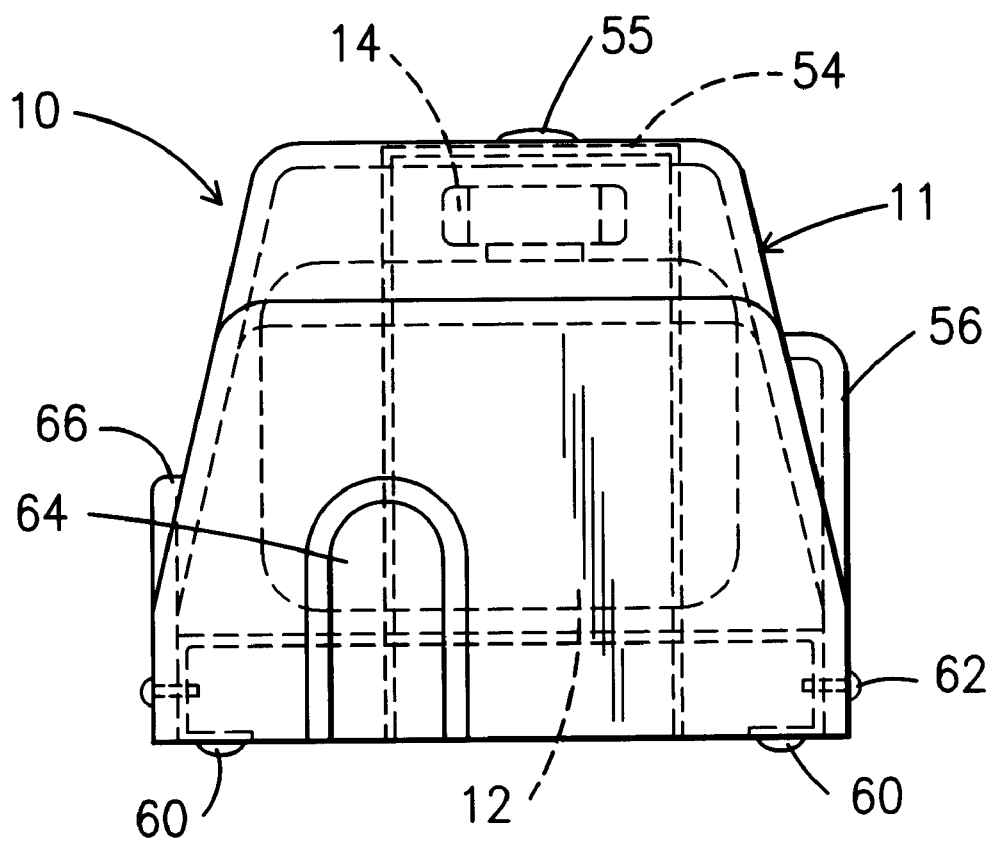
FIG. 4 end view of the inventive dosing device according to FIG. 2.
Figure 5:
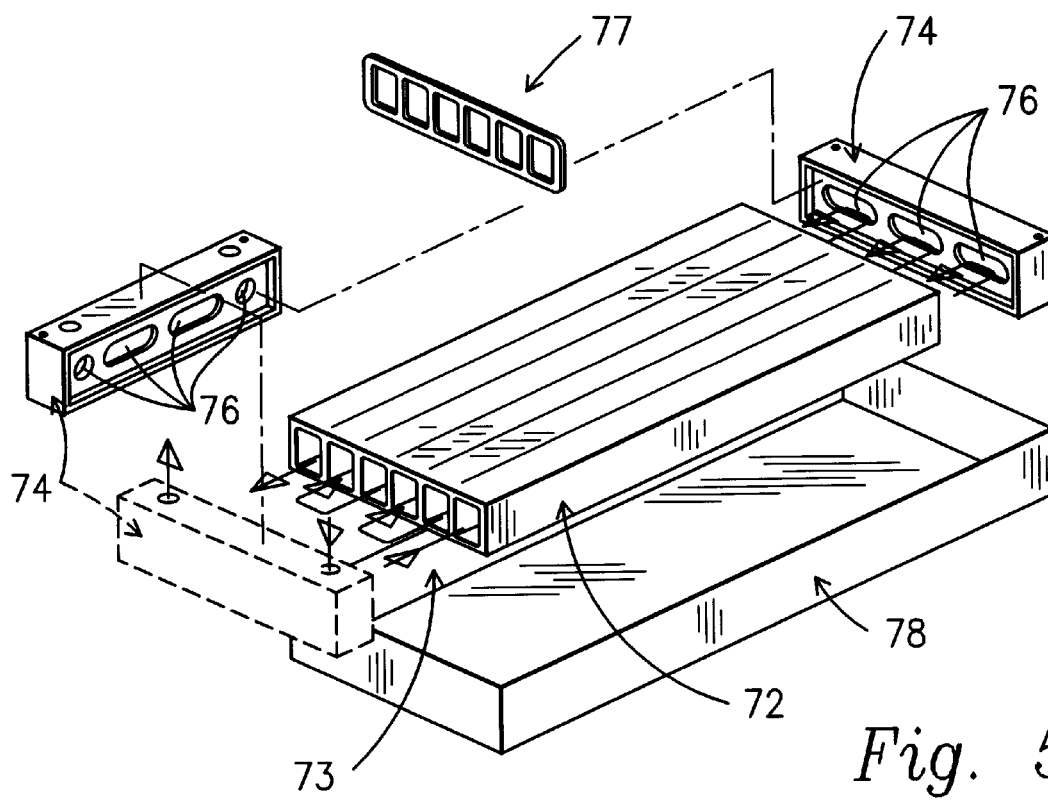
FIG. 5 buffer storage as add-on module.
Figure 6:
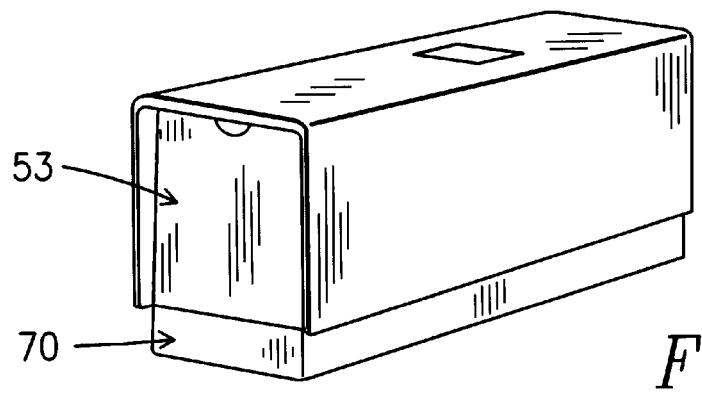
FIG. 6 dosing device with buffer storage.

On the side opposite to the folding lid 54, which in FIG. 4 is shown as a side view, as well as on the side of the housing 11 lying opposite to the control panel 56, there is respectively one special opening 64, 66 provided as so-called hose port, through which the supply lines 17, 19 for the pressurized air as well as for water are introduced. In FIGS. 5 and 6 the construction or design of a buffer storage 70 is represented. It is comprised of a flat tube packet 72, which is formed of multiple, adjacent to each other lying tubes 71 with rectangular cross-section. For forming a through-going flow path 73 end pieces 74 are provided on the end surfaces, which respectively exhibit through-holes 76 of such a design, that fluid tight, pair-wise connections between respectively two adjacent pipes 71 are provided. Seals 77 are provided between the end pieces 74 and the tube packet 70.

The so constructed buffer storage 70 is seated in a receptacle housing 78, which can be situated immediately adjacent to the housing 53 of the dosing device, as shown in FIG. 6. Likewise it is also possible, with appropriate other design and construction of the housing 78, to employ the buffer storage 70 downstream of the dosing device.

Reference Number List

10 Dosing device
Supply container
Signal line (fill condition)
Fill junction pipe with strainer
Pressurized air connection pipe
Pressurized air line
15 Outlet connection pipe
Water supply line
Supply or introduction line
Control line (first supply valve)
First supply valve
20 First supply line
Water conduit, flow path
Control line (water valve)
Water valve
First introduction point
25 Junction point
Flow meter
Signal line
Second introduction point
Second supply line
30 Second supply valve
Control line (second supply valve)
Pressure air valve
Exhaust valve
Pressurized air regulator
35 Manometer
Fine strainer
Back flow valve
Branching
Electrical supply line
40 Control unit
Housing
Folding lid
Screw lock
Panel
45 Light indicators (LED)
Model identification plate
Base feet
Securing screws
Hose port
50 Hose port
Buffer storage
Tube
Tube packet
Flow path
55 End piece
Through-holes
Seal
Receptacle housing

What is claimed is:
1. Dosing device for addition of germicidal or disinfecting material in a supply device for preparing sterilized water for users, comprising:
   a supply container (12) for germicide or disinfectant, said supply container charged with compressed air to pressurize said germicide or disinfectant,
   a flow path (24) for water, which flows to at least one junction point (30), a conduit connecting said supply container to said flow path for water, a proportional valve 22 provided in said conduit between said supply container and said flow path for water, a control unit (52) for controlling said proportional valve, which control unit works in cooperation with a flow meter, which detects the flow volume of the water in the flow path for water and transmits this as a signal to the control unit (52), and which control unit controls the proportional valve to introduce said germicide or disinfectant into the water at a predetermined concentration.

2. Dosing device according to claim 1, wherein the proportional valve (22) is a piezoelectric valve.

3. Dosing device according to claim 1, wherein the concentration of germicide or disinfectant in the flow path for water is variably adjustable between 0% and 100%.

4. Dosing device according to claim 1, wherein a device for sensing the actual concentration of germicide or disinfectant in the flow path for water is connected to the control unit (52) in a closed feed back loop.

5. Dosing device according to claim 1, further including a device for self calibration of the control device.

6. Dosing device according to claim 1, wherein the germicide or disinfectant is introduced into the flow path (24) of the water upstream of the flow meter (32).

7. Dosing device according to claim 1, wherein the flow meter (32) is comprised of at least one rotational body which stirs the supplied water and the introduced germicide or disinfectant and thereby mixes these thoroughly with each other.

8. Dosing device according to claim 1, wherein the germicide or disinfectant is introduced into the flow path (24) of the water at a point (28) which is close to the junction point (30).

9. Dosing device according to claim 1, wherein between the point (28) of the introduction of the germicide or disinfectant into the flow path (24) of the water and the supply container (12) a back flow valve (48) is provided, which prevents entry of water into the supply container (12).

10. Dosing device according to claim 8, wherein between the point (28) of the introduction of the germicide or disinfectant into the flow path (24) of the water and the supply container (12) a filtering device (46) is provided which prevents introduction of impurities from the supply container.

11. Dosing device according to claim 1, wherein for the introduction of the germicide or disinfectant into the flow path (24) of the water a second introduction point (34) with a second supply valve (38) is provided, which operates parallel to the valve (22) first and makes possible a more rapid introduction of the germicide.

12. Dosing device according to claim 1, further including a downstream connected buffer storage (70) for disinfected water in said flow path.

13. Dosing device according to claim 12, wherein the buffer storage (70) is comprised of a tube packet (72), which for the formation of a through going flow path (73) is provided respectively with end pieces (74), wherein the end pieces (74) exhibit through holes (76) which form a fluid tight pair-wise connection between respectively adjacent pipes (71).

14. Dosing device according to claim 12, wherein the buffer storage (70) is provided in a receptacle housing (78) and is formed as a supplemental module, which can be provided immediately adjacent to a housing (53) of the dosing device or connected downstream of the dosing device.

15. Dosing device according to claim 1, wherein said dosing device is constructed as an add-on module, which can be retrofitted into an existing apparatus for dental hygiene.

16. A method for treating water, comprising:

(a) providing germicide or disinfectant into a supply container (12), the supply container in communication with a source of pressurized air via a valve, the supply container further in communication with a water flow path via a proportional valve (22), (b) introducing air from said source of pressurized air into said container to pressurize the contents of said container, (c) sensing the rate of water flow through the water flow path with a flow meter and establishing a signal, (d) sending the signal from step (c) to a control unit (52), (e) sending a signal from control unit (52) to control the degree of opening of the proportional valve (22) as necessary to introduce germicide or disinfectant from the pressurized supply container into the water in the water flow path to maintain a predetermined concentration of germicide or disinfectant in said water flow path.

17. A method as in claim 16, wherein said water flow path flows through an apparatus for dental hygiene.

\* \* \* \* \*